United States Patent [19]
Kowalski et al.

[11] Patent Number: 6,093,348
[45] Date of Patent: *Jul. 25, 2000

[54] PROCESS FOR MANUFACTURE OF CAROTENOID COMPOSITIONS

[75] Inventors: Ray Edward Kowalski, Morris Plains; William Joseph Mergens, West Caldwell; Leonard Joseph Scialpi, Andover, all of N.J.

[73] Assignee: Roche Vitamins Inc., Nutley, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/854,571

[22] Filed: May 12, 1997

Related U.S. Application Data

[60] Provisional application No. 60/017,568, May 14, 1996.

[51] Int. Cl.⁷ .............................. B01F 3/20; A23L 1/303; C08K 5/00
[52] U.S. Cl. .................. 252/363.5; 516/31; 516/924; 426/73; 426/540; 514/725; 106/498
[58] Field of Search ..................................... 252/303, 314, 252/363.5; 516/31, 924; 426/73, 540; 514/168, 725; 8/526; 106/498

[56] References Cited

U.S. PATENT DOCUMENTS

| | | | |
|---|---|---|---|
| 2,756,177 | 7/1956 | Cannalonga et al. | 264/109 |
| 2,861,891 | 11/1958 | Bauernfeind et al. | 426/540 |
| 3,998,753 | 12/1976 | Anoshkiw et al. | 252/312 |
| 4,435,427 | 3/1984 | Hoppe et al. | 424/356 |
| 4,522,743 | 6/1985 | Horn et al. | 252/311 |
| 4,533,254 | 8/1985 | Cook et al. | 366/176.1 |
| 4,908,154 | 3/1990 | Cook et al. | 252/314 |
| 5,364,563 | 11/1994 | Cathrein et al. | 252/311 |
| 5,460,823 | 10/1995 | Jensen et al. | 426/73 |
| 5,700,471 | 12/1997 | End et al. | 252/303 |
| 5,863,953 | 1/1999 | Lueddecke et al. | 514/691 |

FOREIGN PATENT DOCUMENTS

| | | |
|---|---|---|
| 1330270 | 6/1994 | Canada . |
| 065 193 | 5/1982 | European Pat. Off. . |
| 0 266 323 | 5/1988 | European Pat. Off. . |
| 0 276772 | 8/1988 | European Pat. Off. . |
| 1211911 | 8/1960 | Germany . |
| 43 29 446 | 3/1995 | Germany . |
| 91/06292 | 5/1991 | WIPO . |
| 94/19411 | 9/1994 | WIPO . |

OTHER PUBLICATIONS

Derwent Abstract of EP 0 276 772, Database WPIL, week 8831, London;Derwent Publications Ltd., AN88–214192, Class B04, (BASF AG), abstract.

*Primary Examiner*—Richard D. Lovering
*Assistant Examiner*—Daniel S. Metzmaier
*Attorney, Agent, or Firm*—Mark E. Waddell; Stephen M. Haracz; Bryan Cave LLP

[57] ABSTRACT

A method for the manufacture of carotenoid powders is disclosed. In the disclosed method, an aqueous suspension of the carotenoid is heated to melt the carotenoid, the suspension is then homogenized under pressure to form an emulsion, and the resulting emulsion is dried to obtain the carotenoid powder.

8 Claims, 2 Drawing Sheets

PROCESS FOR MANUFACTURE OF CAROTENOID COMPOSITIONS

BACKGROUND OF THE INVENTION

This application claims priority to provisional application Ser. No. 60/017,568 filed May 14, 1996.

βCarotene as well as other carotenoids such as e.g. lycopene, bixin, zeaxanthin, cryptoxanthin, lutein, canthaxanthin, astaxanthin, β-apo-8'-carotenal, β-apo-12'-carotenal as well as esters of hydroxy-and carboxy-containing compounds of this group, e.g., the lower alkyl esters, preferably the methyl ester and ethyl ester, have, acquired a considerable significance as colorants or color-imparting agents for foodstuffs or also as feed additives. More recently, it has been suggested that β-carotene is effective as a prophylactic against cancerous diseases.

However, carotenoids are substances which are insoluble in water, have high melting points and are also sensitive to heat and oxidation. These properties of carotenoids are especially disadvantageous in the coloring of aqueous media, since it is extremely difficult, because of their water-insolubility, to achieve a homogeneous or sufficiently intense coloring effect.

In the case of β-carotene (BC) these properties, especially the water-insolubility, give rise to extremely poor bioavailability from pharmaceutical dosage forms such as, for example, tablets, capsules etc. which contain this carotenoid. The aforementioned properties are, moreover, an obstacle to a direct use of crystalline β-carotene for the coloring of aqueous foodstuffs, as feed additives, or also for use as a source of vitamin A, since crystalline β-carotene is absorbed only poorly or imparts only a poor coloring effect.

Various processes for the manufacture of water-dispersible carotenoid compositions are already known from the literature, but these are all associated with certain disadvantages. Thus, for example, from German Patent No. 1 211 911 it is known to manufacture carotenoid compositions by dissolving a carotenoid in a carotenoid solvent, emulsifying the resulting solution into an aqueous solution of a protective colloid and subsequently removing the solvent from this emulsion. The disadvantage of this process resides in the fact that chlorinated hydrocarbons are preferably used as the solvent and their removal creates an environmental burden which makes the process extremely expensive from a commercial point of view. Furthermore, it is known from European Patent No. 65 193 to manufacture carotenoid compositions by dissolving a carotenoid in a non-chlorinated volatile water-miscible organic solvent at temperatures between 50° and 200° C. within a period of less than 10 seconds, precipitating the carotenoid in colloid-dispersed form from the solution obtained by mixing with a solution of a colloid and subsequently removing the solvent. Here also an organic solvent must therefore be removed, which again is expensive on an industrial scale.

Alternatives to the use of organic solvents are well known. For example, IPN WO 91/06292 describes a process for milling of the carotenoid crystal in an aqueous medium. However, while the stability of the resultant powders are good, their tinctorial power in aqueous solutions and thus their bioavailability, are poor due to the coarse size of the carotenoid particle relative to that obtained with sub-micron emulsion techniques. Other methods, for example U.S. Pat. No. 2,861,891, include the use of solubilizing oils to effect the desired particle size reduction. The use of the solubilizing oils is limited where, for example, there are concerns about the healthiness of the various oils, and where the manufacture of higher potency powders is desired, due to the limited solubility of the carotenoids, even when the oils are rendered supersaturated with carotenoid at elevated temperatures.

There accordingly exists a need for a process for the manufacture of higher potency powdered carotenoid compositions which is carried out without the use of organic solvents and/or solubilizing oils and which compositions are readily dispersible in aqueous media and which, moreover, in the case particularly of β-carotene, are suitable for the manufacture of pharmaceutical dosage forms having good stability and bioavailability of the active substance.

SUMMARY OF THE INVENTION

The present invention comprises a novel process for the manufacture of colloid-dispersed carotenoid compositions and the thus manufactured compositions themselves. The compositions manufactured in accordance with the invention are useful, depending on the carotenoid which is used, not only for the manufacture of pharmaceutical dosage forms, but also for the coloring of foodstuffs and as feed additives.

By means of the process in accordance with the invention, it is now possible to avoid the aforementioned disadvantages and to obtain carotenoid compositions having the heretofore unattainable properties. We have discovered that carotenoid powders having a potency of up to 25% (potency being the percentage, by weight, of the carotenoid in the final composition) and having high tinctural power (and thus having the related high bioavailability) can be obtained by carrying out the present high temperature/high pressure (HTHP) process without the need for solubilizing oils or organic solvents. The resulting powders have excellent stability (shelf-life) and bioavailability in tablet applications.

The method of the invention comprises melting the carotenoid, for example β-carotene, within an aqueous suspension of the carotenoid and a protective colloid by heating the suspension to 180° C. to 250° C., preferably to 180° C. to 225° C., more preferably to 185° C. to 195° C., and homogenizing the suspension containing the melted carotenoid at a pressure of 1,400 to 40,000 psi, preferably 1,400 to 15,000 psi, more preferably 2,000 to 10,000 psi, to obtain an emulsion, and drying the emulsion to obtain the carotenoid powder.

DETAILED DESCRIPTION OF THE INVENTION

Figure 1:
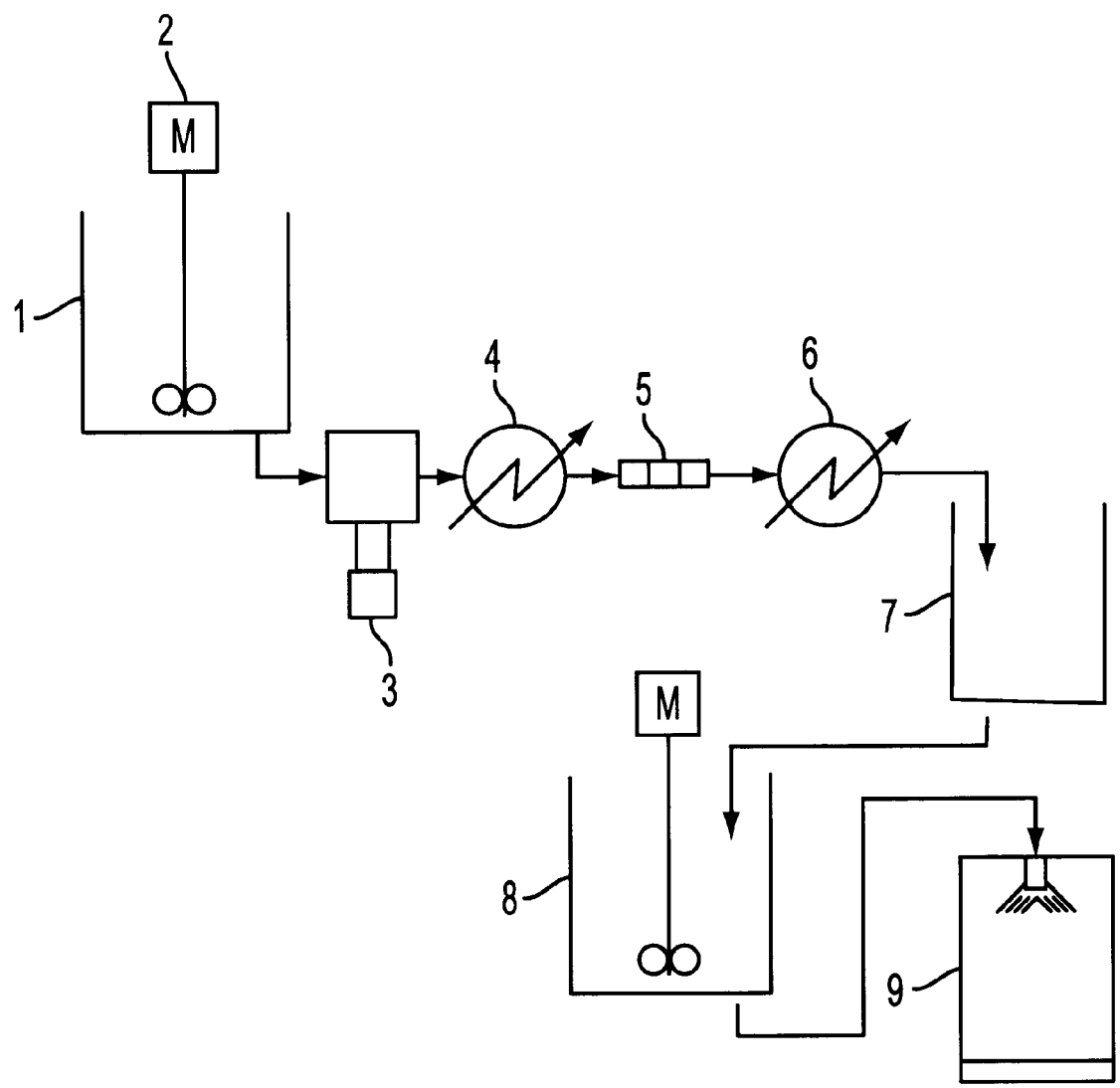
FIG. 1 shows a schematic for processing carotenoid crystals by the high temperature/high pressure (HTHP) process in accordance with the invention. The residence time of the carotenoid crystals in the Heat Exchanger was designed to be <60 seconds for melting of the carotenoid crystals.

The present invention comprises a novel high temperature/high pressure (HTHP) process which is capable of producing high potency (up to 25% by weight) carotenoid powders (the powder particles themselves are referred to as "beadlets") having excellent tablet stability and bioavailability, without the need for carotenoid solubilizing oils or organic solvents, although their use is not precluded. The beadlets comprise a matrix of a protective colloid, such as gelatin, with the carotenoid dispersed therein. Preferably, the matrix also comprises a plastisizer, such as a sugar. The process in accordance with the invention provides carotenoid beadlets in which the mean particle size of the carotenoid particles within the beadlet matrix are in the range from 0.1 to 0.5 microns, as measured by conventional laser light scattering instruments, such as a Malvern Zetasizer (Malvern Instruments Inc., Southborough, Mass.).

The method of the invention comprises melting the carotenoid within an aqueous "feed" suspension containing the carotenoid, a surfactant and optionally a protective colloid by heating the suspension to 180° C. to 250° C., preferably to 180° C. to 225° C., more preferably to 185° C. to 195° C., and homogenizing the suspension containing the melted carotenoid at a pressure of 1,400 to 40,000 psi, preferably 1,400 to 15,000 psi, more preferably 2,000 to 10,000 psi, to obtain a carotenoid emulsion, and drying the emulsion to obtain the final composition, a carotenoid powder.

In accordance with the invention, it is preferred to cool the carotenoid emulsion immediately after homogenization by adding an aqueous "Addition Matrix." Such Addition Matrix contains a plasticizer, and may also contain additional protective colloid, antioxidants, microbial preservatives, and the like, for including in the final composition. The plasticizer in the Addition Matrix also acts to avoid the deleterious effects of high temperature, e.g., carmelization and the formation of maillard products.

The preferred compounds for use with the process of the invention are the carotenoids. Examples of carotenoids are β-carotene, lycopene, bixin, zeaxanthin, cryptoxanthin, lutein, canthaxanthin, astaxanthin, β-apo-8'carotenal, β-apo-12'-carotenal, 2'-dehydroplectaniaxanthin, as well as esters of hydroxy-and carboxy-containing compounds of these compounds, e.g. the lower alkyl esters, preferably the methyl ester and ethyl ester. The especially preferred compound for use in the process of the invention is β-carotene. While the claimed process is described for processing carotenoids, especially β-carotene, one skilled in the art could apply the disclosed process to other compounds having similar physical and chemical properties with only routine changes in processing conditions. Examples of other compounds are drugs and the fat-soluble vitamins, especially vitamin A and its derivatives.

Any conventional homogenizing device which is capable of operating under the temperature and pressure requirements of the present process may be used to practice the process of the invention. An example of such a conventional homogenizing device is a Rannie High Pressure Homogenizer (APV Corp., Wilmington, Mass.).

The preferred homogenizing devices for practicing the process of the invention are those disclosed in U.S. Pat. Nos. 4,533,254 ('254 patent) and 4,908,154 ('154 patent), the disclosures of which are hereby incorporated by reference.

The especially preferred homogenizer is a device of the '254 patent manufactured by Microfluidics Corp., Newton, Mass., under the name MICROFLUIDIZER. A recycling of the aqueous suspension in the homogenizing device as described in the aforementioned patents may be done to reduce the size of the dispersed carotenoid droplets and/or to make them of more uniform size.

The concentration of the caroteniod in the aqueous feed suspension depends on the respective carotenoid which is used and on the intended use of the end product. Concentrations of carotenoid in the aqueous feed suspension which provide a potency in the range from 10% to 25% by weight of the final composition are preferred.

The carotenoid feed suspension also contains a surfactant. Any conventional surfactants, as is known to those skilled in the art, such as for example sorbitan derivatives, glycerol monostearate, citric acid esters and ascorbic acid 6-palmitate, etc. may be used in accordance with the invention. The amount of surfactant is typically 0.1 to 6.0% by weight based on the final composition and more preferably, 2 to 4% by weight. The preferred surfactant is ascorbyl palmitate (which also functions as an antioxidant) and is especially preferred when the carotenoid feed suspension has a pH of 6.5–7.5.

In addition to a carotenoid or a mixture of two or more carotenoids, and the surfactant, the aqueous feed suspension preferably contains a protective colloid in an amount from 5% to 75% by weight of the final composition. Any conventional protective colloids, as is known to those skilled in the art, such as gum acacia, gelatin, milk and vegetable proteins, starch and starch derivatives, etc., may be used in accordance with the invention. The preferred protective colloid is gelatin, from either fish or mammalian sources, having a bloom of 0 to 300.

All of the protective colloid need not be contained in the feed suspension. A portion may be added subsequent to the homogenization step as part of the Addition Matrix which is preferably added to the aqueous suspension to cool it immediately after homogenization. The amount of protective colloid in the feed suspension may range from about 10–30% by weight, preferably about 20% by weight, of total protective colloid in the final composition. The preferred ratio for the distribution of protective colloid between the feed suspension and the Addition Matrix is 1:1 to 1:9 and more preferably, 1:2 to 1:5.

Because carotenoids are subject to oxidation, the preparation of the carotenoid suspension is performed under an inert gas, e.g., nitrogen, and the suspension may also contain conventional antioxidants. The antioxidants preferred for β-Carotene are 1–8% by weight of sodium ascorbate, preferably 2–4% by weight, 0.1–6% by weight of ascorbyl palmitate, preferably 2–4% by weight, and 0.5–4% by weight of dl-alpha tocopherol, preferably 1–2% by weight, all based on a final composition having 10–25% by weight β-Carotene content. Antioxidants for other carotenoids and other compounds useful in the process of the invention are known to those skilled in the art. Examples are propyl gallate, BHT and BHA. The suspension may also contain any conventional antimicrobial preservatives, such as the sorbates, parabens, benzoic acid, etc., in amounts that are conventionally used.

After the carotenoid in the feed suspension is melted and the feed suspension is homogenized, the resulting emulsion is preferably further processed by adding to the emulsion the Addition Matrix which contains the remaining protective colloid (if any) and a plasticizer so that the final composition desired may be achieved upon drying. Any conventional plasticizer, as is known to those skilled in the art, such as for example sugars, sugar alcohols, glycerin, etc., may be used in accordance with the invention. The preferred plasticizer is sucrose. When gelatin is the protective colloid, the ratio of gelatin to plasticizer in the final composition is in a range from 5:1 to 1:5 and preferably in the range from 2:1 to 1:2.

The completed carotenoid emulsion is converted into a dry, stable, powder form using any conventional means, as is known to those skilled in the art, such as spray drying, fluidized spray drying, or beadlet technology such as the oil suspension or starch catch methods known in the art. The preferred method of converting the emulsion to a dry powder is starch catch beadlet technology, such as that described in U.S. Pat. No. 2,756,177.

The invention hereinafter shall be described with respect to the preferred compound for use with the invention, β-carotene (BC). This description is meant to exemplify, and not limit, the scope of the invention.

In accordance with the invention, the aqueous BC feed suspension is heated under pressure (with the pressure being at least sufficient to prevent boiling of the water) under conditions sufficient to melt the BC within about 1–60 seconds, preferably from 1–30 seconds, and then instantly homogenized in the homogenizing device. Preferably, the aqueous BC suspension is pressurized and then heated. Prior to processing the BC suspension and concurrent to the preparation of the BC suspension, the system is preferably first equilibrated on water to the required temperature and pressure. Flushes of dilute protective colloid solution may also be passed through the unit both prior to and immediately after the BC suspension, as a precautionary measure to prevent BC crystal formation and subsequent clogging of the device.

In order to minimize degradation and to control isomerization of the carotenoid so as to obtain the isomers most preferable for the intended biological effect, it is necessary to control the amount of time the carotenoid suspension is maintained at high temperatures ("residence time"). This is readily done in the design of the heat exchanger(s) by taking into consideration the size and volume of the heating surface, the suspension throughput, the temperature and pressure desired and the type of heat transfer media employed. Residence times of less than 60 seconds at temperatures above the melting point of BC are desirable, with residence times of less than 30 seconds at that temperature preferred. Most preferable are residence times of less than 30 seconds at temperatures which preclude isomeration but raise the suspension to temperatures that approach the melting point of BC, immediately followed by residence times of <3 seconds at temperatures at or above the melting point of BC. To further minimize the effects of high temperatures on the newly formed BC emulsion which exits the homogenizing device, it is desirable to add the Addition Matrix, i.e., protective colloid and/or plasticizers, having a temperature of 25–70° C. to rapidly cool the hot emulsion, which is then further cooled in a heat exchanger to temperatures which are suitable for processing into a dry powder.

Additionally, to minimize the exposure time of BC to the potential effects of high temperatures, it is advantageous to use BC where 90% of the particles, D[V,0.9] as measured by laser light scattering, are less than 30 microns. Preferably, it is desired to use BC having a particle size, D[V,0.9], of less than 3 microns. When BC crystals of a particle size less than 3 microns are not available, it is preferred to obtain such by milling larger BC crystals to that smaller size. This is readily accomplished by passing the aqueous suspension of BC through, for example, a ball mill, repeatedly, if necessary, until the desired particle size is obtained.

The entire process can be carried out either in a continuous or batchwise mode. The process in accordance with the invention can be carried out, for example in apparatus as are shown in FIG. 1 and FIG. 2.

FIG. 1 shows an apparatus for carrying out the present invention. In a suitable size stainless steel vessel (1), carotenoid crystals (90% of the particles having a size of less than 30 microns) are first suspended by high shear mixing (2) in an aqueous solution of a surfactant, which may also contain protective colloid, microbial preservatives and antioxidants. This carotenoid feed suspension is then pressurized via a pneumatically powered pump (3) and processed, first through a helical coil type heat exchanger (4), whose temperature is controlled by circulating hot oil to the shell side of the unit, to melt the crystals in a short time (<60 seconds), and then through an interaction chamber (5) where homogenization occurs instantaneously, resulting in a submicron carotenoid emulsion. The emulsion is then cooled (60'–85° C.) by passage through a second heat exchanger (6) and collected in a suitable container (7). The resulting emulsion is further processed by mixing with the Addition Matrix containing the remaining protective colloid (if any), a plasticizer and any antioxidants to achieve the desired formula which will have the desired composition and potency upon drying. The "Addition Matrix" is prepared in parallel in a suitable size vessel equipped with a high shear mixer (8). The completed emulsion is then converted into a dry, stable, final carotenoid powder form using conventional starch catch beadlet technology (9).

Figure 2:
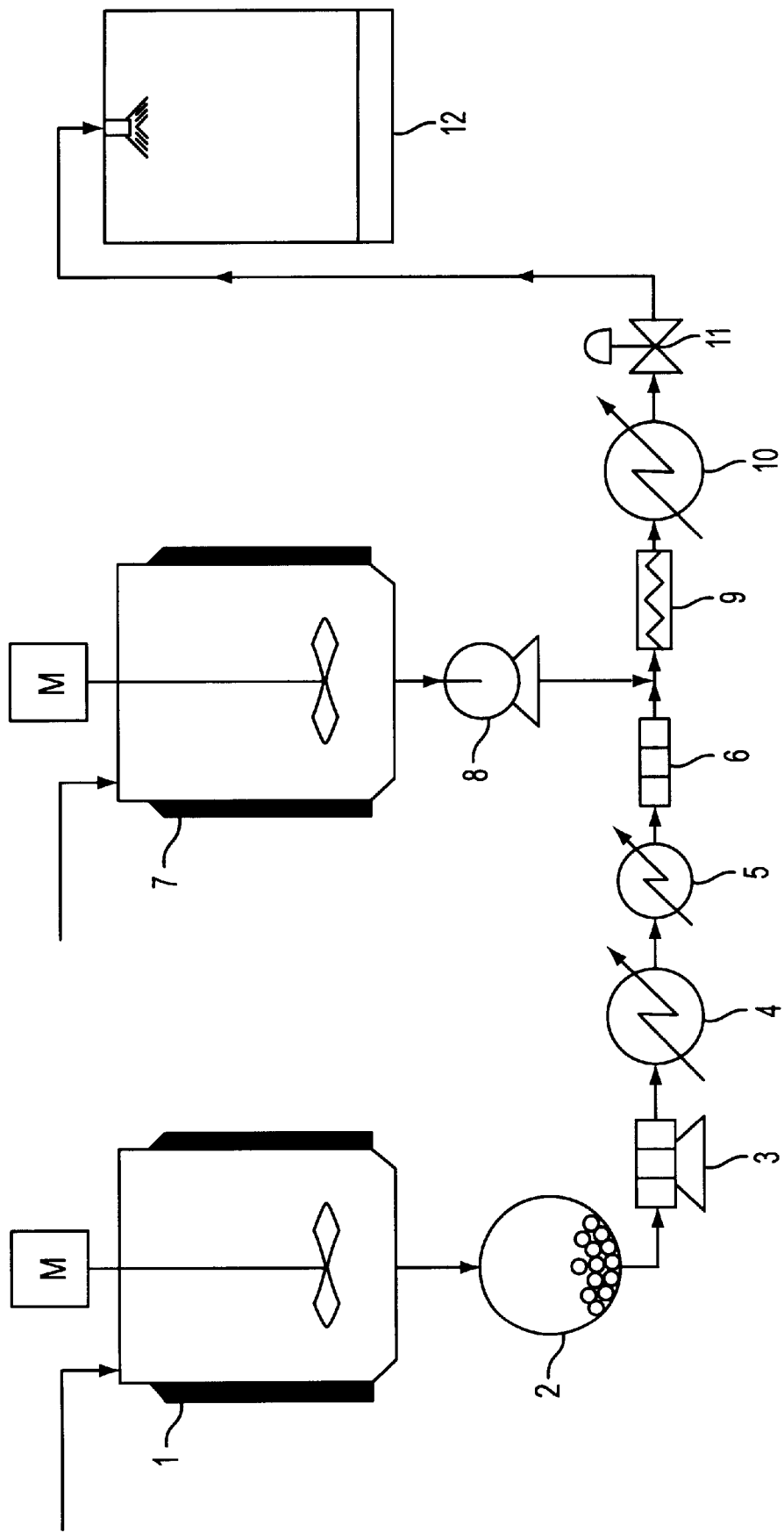
FIG. 2 shows a schematic for processing carotenoid crystals by the HTHP process which was designed with a primary heat exchanger and a smaller secondary heat exchanger in series and having residence times of the carotenoid crystals in the heat exchangers of <30 and <3 seconds, respectively.

FIG. 2 shows a further embodiment of the process scheme for carrying out the present invention. The aqueous feed suspension of a carotenoid is prepared under an inert atmosphere in a suitable size jacketed stainless steel vessel equipped with an agitator (1). The suspension contains a surfactant, and optionally protective colloid, microbial preservatives and antioxidants. The suspension is milled in a ball mill (2) until 90% of the carotenoid particles have a size of less than 3 microns. The milled suspension is then metered with a high pressure pump (3) into the first heat exchanger (4) where the temperature of the suspension approaches the melting point of the particular carotenoid, then into the second heat exchanger (5) wherein the carotenoid is completely melted. The residence time in these two helical coil type heat exchangers is <30 and <3 seconds, respectively. The temperatures of the heat exchangers are controlled by regulating the steam pressure on the shell side of the units. The solution then passes through a high pressure homogenizing device (6) where a submicron emulsion of the carotenoid is produced. In parallel to these events, the aqueous "Addition Matrix," which may contain protective colloids, plasticizers, antioxidants and microbial preservatives, is prepared in a suitable size jacketed stainless steel vessel equipped with an agitator (7) and then metered with a pump (8) at such a rate as to achieve the desired formula composition and potency. The streams from the Addition Matrix and the carotenoid emulsion are then combined in a static mixer (9) where they become homogeneous prior to being cooled in a heat exchanger (10). The emulsion pressure is then reduced to atmospheric as it passes through a pressure control valve (11) and the completed emulsion is then converted into a dry, stable, final carotenoid powder form by using conventional starch catch beadlet technology (12).

EXAMPLE 1

For the preparation of a 20% β-Carotene Powder:

A. Prepare Beta Carotene Feed Suspension

Add the water, then the following ingredients to a suitable size stainless steel pot, mix, and place the pot in a water bath (ca 70°–80° C.) for 1–2 hours to hydrate the gelatin.

| | gm |
|---|---|
| Gelatin (140 bloom) | 286.4 |
| Sodium Benzoate | 20 |
| Sorbic Acid | 7.5 |
| Methyl Paraben | 3.25 |
| Propyl Paraben | 0.38 |
| Sodium Ascorbate | 5 |
| Distilled Water | 1755 |

Add 50 gm ascorbyl palmitate in portions to the gelatin solution while mixing with a suitable high shear mixer (e.g., Gifford-Wood) to ensure uniform distribution. Adjust the mixture to pH 7.2–7.8 with 20% w/w sodium hydroxide solution. While mixing with the high shear mixer, slowly add 50 gm dl-alpha tocopherol and 575 gm β-carotene crystals to the mixture. The particle size of the BC crystals, as determined by a Malvern Mastersizer X Particle Size Analyzer, was 90% less than 30 microns. Re-adjust pH to 7.2–7.8 (if necessary). Hold the beta carotene suspension in a water bath (70–80° C.) until ready to process further. Re-mix the suspension just prior to processing so as to ensure homogeneity.

B. Prepare Beta Carotene Emulsion

Equilibrate the system (FIG. 1) with distilled water to obtain the desired pressure and temperature. The temperature of the circulating fluid in the oil heating unit is first adjusted to ensure that the process is operated at the target conditions. A MICROFLUIDIZER Model M110ET is used as the homogenizing device.

Feed Suspension Inlet Temp: 210–215° C.

Emulsion Outlet Temp: 60° C.

Pressure: 6000 psi

When equilibrated, begin feeding the BC suspension to the intake of the pump. Collect beta carotene emulsion in a suitable container.

C. Prepare and add Addition Matrix to Emulsion

Only a portion, 2000 gm, of the beta carotene emulsion produced in step B is used for further processing. In a manner similar to step A, prepare and then add the Addition Matrix to the BC emulsion, mix and then (if necessary) adjust pH to 6.8–7.2 with 20% sodium hydroxide solution.

| Addition Matrix | gm |
|---|---|
| 47% w/w Gelatin Solution | 401.6 |
| Sucrose | 374.7 |
| Sodium Ascorbate | 66.6 |
| Distilled Water | 108 |

D. Prepare Powder

The completed emulsion is then converted into a dry powder by spraying into a bed of chilled starch, subsequently separated by sieving and the resulting powder then dried to a moisture content of 5–6% in a fluid bed dryer.

EXAMPLE 2

A. The powder produced in Example 1 has the following mesh profile as determined by sieve analysis (U.S. Standard).

Wt % on 40 mesh 0.1
50 mesh 3.5
60 mesh 17.5
80 mesh 77.1
100 mesh 0.8
Pan 1.0

B. A sample of this powder was re-dispersed with moderate agitation in warm distilled water, and found to impart significant color to the solution. An indication of this good tinctorial power is the determination of the $E_1^1$ value* which was found to be 1147.

* Procedure as shown in Example 8, which is a standard measure of absorptivity.

EXAMPLE 3

A. Stability results for the powder, per se, and in two different tablet applications are shown below:

| | Per Se | Multivitamin + Iron* | Multivitamin + Minerals* |
|---|---|---|---|
| Initial BC Assay | 19.3% | 4.1 mg/tablet % BC Retention (Based on initial assay) | 0.8 mg/tablet |
| Storage Conditions: | Rentension (%)** | Rentension (%)** | Rentension (%)** |
| 45° | | | |
| 1 month | 98 | | |
| 3 months | 95 | | |
| 6 months | 97 | | |
| RT | | | |
| 1 month | 96 | 98 | 121 |
| 3 months | 98 | 95 | 118 |
| 6 months | 98 | 95 | 119 |
| 9 months | 99 | 100 | 101 |

*Formulation and tablet procedures are as described in Examples 7 and 8.
**Analysis by HPLC

EXAMPLE 4

β-Carotene powders of different compositions were prepared according to the following in a manner analogous to Example 1 (Expt. 1).

| | Expt. 1 | Expt. 2 | Expt. 3 | Expt. 4 |
|---|---|---|---|---|
| Ratio Gelatin in Feed Suspension to Addition Matrix | 1:1 | 1:1 | 1:4.2 | 1:0 |
| Ratio Gelatin to Sucrose in Final Powder | 1:1 | 1:2 | 1:1 | 1:1 |
| BC Suspension: | Grams | | | |
| Gelatin (140 Bloom) | 286.4 | 403.0 | 173.2 | 915.9 |
| Sodium Benzoate | 20.0 | 32.0 | 24.0 | 24.0 |
| Sorbic Acid | 7.5 | 12.4 | 9.3 | 9.3 |
| Methyl Paraben | 3.25 | 5.2 | 3.9 | 3.9 |
| Propyl Paraben | 0.38 | 0.56 | 0.42 | 0.42 |
| Sodium Ascorbate | 5.0 | — | — | — |
| Distilled Water | 1755 | 2342 | 1546 | 2855 |
| Ascorbyl Palmitate | 50.0 | 52.0 | 39.0 | 39.0 |
| 20% w/w NaOH Solution | Adjust pH to 7.2 to 7.8 | | | |
| dl-Alpha Tocopherol | 50.0 | 72.0 | 54.0 | 54.0 |
| BC Crystals | 575.0 | 720.0 | 543.9 | 543.9 |
| Addition Matrix: | | | | |
| Gelatin Solution (47% w/w) | 401.6 | 550.2 | 791.6 | — |
| Sucrose | 374.7 | 1023.4 | 459.8 | 592.3 |
| Sodium Ascorbate | 66.6 | — | — | — |
| Distilled Water | 108. | 595 | — | — |

-continued

|  | Expt. 1 | Expt. 2 | Expt. 3 | Expt. 4 |
| --- | --- | --- | --- | --- |
| 20% w/w NaOH Solution | Adjust pH to 6.8–7.2 (If Necessary) | | | |
| Weight Emulsion Mixed with Additional Matrix: | 2000 | 2423 | 1300 | 3100 |
| Process Conditions: | | | | |
| Pressure (psi) | 6000 | 10,000 | 10,000 | 2500 |
| Inlet Temperature (° C.) | 213–227 | 222 | 213–215 | 195–197 |
| Flow Rate (gm/min) | 578 | 740 | 670 | 320 |
| Outlet Temperature (° C.) | 62–68 | 78 | 80 | 71–72 |
| Powder Characteristics: | | | | |
| Particle Size, Internal Phase, Mean Diameter | 235 nm | 190 nm | 272 nm | 259 nm |
| BC Content (HPLC Assay) | 19.3% | 18.4% | 16.4% | 16.4% |
| -Trans BC Content | 45% | 33% | 36% | 35% |

EXAMPLE 5

Lycopene powders were also prepared and in a manner analogous to Example 1. Compositions had a gelatin to sucrose ratio of 1:1 and were formulated with and without oil (peanut).

|  | Expt. 5 | Expt. 6 |
| --- | --- | --- |
| Ratio Gelatin in Feed Suspension to Addition Matrix: | 1:1 | 1:3.1 |
| Lycopene Suspension: | Grams | |
| Fish Gelatin | 95.9 | 67.5 |
| Distilled Water | 571.5 | 1343 |
| Ascorbyl Palmitate | 20.0 | 30.0 |
| 20% w/w NaOH Solution | Adjust pH to 7.2 to 7.5 | |
| dl-Alpha Tocopherol | 15.0 | 22.5 |
| Peanut Oil | — | 45.0 |
| Lycopene Crystals | 120.0 | 180.0 |
| Addition Matrix: | | |
| Fish Gelatin | 54.7 | 47.0 |
| Sucrose | 195.5 | 107 |
| Distilled Water | 44.4 | — |
| Weight Emulsion Mixed with Additional Matrix: | 468.7 | 382 |
| Process Conditions: | | |
| Pressure (psi) | 6000 | 3,000 |
| Inlet Temperature (° C.) | 209–217 | 206 |
| Flow Rate (gm/min) | 387 | 268 |
| Outlet Temperature (° C.) | 40–42 | 47 |
| Powder Characteristics: | | |
| Particle Size, Internal Phase Mean Diameter | 221 nm | 320 nm |
| Lycopene Content (UV) | 8.9% | 7.8% |
| -Trans Lycopene Cont | 46% | 45% |
| Color Intensity (E|) | 851 | 657 |

EXAMPLE 6

The following carotenoid powders were prepared in a manner analogous to Example 1 but with larger batch sizes so as to provide continuous run times of 2½ to 3 hours. For these trials, the process scheme is illustrated by FIG. 2.

|  | Expt. 7 20% BC Powder | Expt. 8 10% BC Powder | Expt. 9 5% 2'DHP Powder |
| --- | --- | --- | --- |
| CAROTENOID FEED SUSPENSION: | Kg/100 Kg | | |
| Beta Carotene | 22.97 | 9.42 | — |
| 2' Dehydroplectaniaxanthin | — | — | 10.4 |
| dl-Alpha Tocopherol | 1.6 | 0.68 | 1.73 |
| Ascorbyl Palmitate | 3.74 | 1.78 | 1.73 |
| Na Ascorbate | 0.24 | — | — |
| Gelatin (140 Bloom) | 6.07 | 22.0 | 13.79 |
| Sodium Hydroxide (28% w/w Sol) | 0.38 | 1.57 | 0.34 |
| Water | 65.0 | 64.55 | 72.0 |
| ADDITION MATRIX: | Kg/100 Kg | | |
| Gelatin (140 Bloom) | 21.7 | — | 22.18 |
| Sucrose | 24.57 | 40 | 11.22 |
| Yellow Dextrin | — | — | 11.22 |
| Sodium Ascorbate | 2.35 | — | — |
| Sodium Hydroxide (28% w/w Sol) | 0.15 | — | 0.21 |
| Water | 51.24 | 60 | 55.18 |
| Operating Conditions: | | | |
| High pressure Homogenizing Device | Micro-fluidics IX*-Chamber | Rannie HP Valve (12.51H) | Micro-fluidics IX*-Chamber |
| Gelatin Distribution Between Suspension and Addition Matrix | 1:3.7 | 1:0 | 1:4 |
| Particle Size Carotenoid D[V,0.9] μm in Suspension | 2.3 | 20 | 3.1 |
| Temperature Suspension (° C.) | 60 | 60 | 60 |
| Temperature Matrix (° C.) | 60 | 60 | 60 |
| Temperature Addition Matrix (° C.) | 50 | RT | 50 |
| Solid Content of Suspension (%) | 35 | 34 | 28 |
| Solid Content of Emulsion (%) | 42 | 36 | 40 |
| Feed Rate Suspension/Matrix (kg/h) | 38 | 50 | 38 |
| Feed Rate Addition Matrix (kg/h) | 39.3 | 27.5 | 94.7 |
| Pressure after HE* 1 (bar) | 190–200 | 460 | 170–190 |
| Pressure after HE 2 (bar) | 190–200 | 460 | 172–180 |
| Temperature after HE** 1 (° C.) | 160 | 130–140 | 160 |
| Temperature middle of HE 2 (° C.) | 195 | 215 | 190 |
| Pressure after Homogenizing Device (bar) | 27 | 27 | 27 |
| Temperature after the Static Mixers (° C.) | 121 | 135 | 92 |
| Temperature at the Emulsion Outlet (° C.) | 60 | 60 | 67–68 |

*IX = Interaction
**HE = Heat exchanger

EXAMPLE 7

| MULTIVITAMIN-MULTIMINERAL TABLETS FORMULATION | |
| --- | --- |
| Ingredients | mg/Tablet |
| 1. Beta carotene 20% Beadlets | 4.50[1] |
| 2. Dry Vitamin E Acetate 50% SD | 63.00 |
| 3. Ascorbic Acid 90% Granulation | 105.00 |
| 4. Folic Acid | 0.50 |
| 5. Thiamine Mononitrate | 2.48 |
| 6. Riboflavin Type S | 2.86 |
| 7. Niacinamide Free Flowing | 21.00 |
| 8. Pyridoxine Hydrochloride | 4.00 |
| 9. Vitamin B12 0.1% SD | 11.70 |
| 10. BITRIT-1 | 5.63 |
| 11. Calcium Pantothenate | 14.67 |

-continued

MULTIVITAMIN-MULTIMINERAL TABLETS FORMULATION

| Ingredients | mg/Tablet |
|---|---|
| 12. Ferrous Fumarate (32.87% Fe) | 82.20 |
| 13. Cupric Oxide (79.88% Cu) | 3.76 |
| 14. Zinc Sulfate Dried (36.43% Zn) | 61.76 |
| 15. Manganese Sulfate Monohydrate (32.5% Mn) | 23.10 |
| 16. Potassium Iodide Stabilized (68% $I_2$) | 0.22 |
| 17. Potassium Chloride (52.4% K) (47/6% Cl) | 14.70 |
| 18. Magnesium Oxide USP/DC E.M. (60% Mg) | 166.67 |
| 19. Dicalcium Phosphate Dihydrate, Unmilled (23.3% Ca) (18.0% P) | 696.00 |
| 20. Modified Food Starch (Explo-Tab) | 70.00 |
| 21. Modified Cellulose Gum (Ac—Di—Sol) | 47.00 |
| 22. Microcrystalline Cellulose (Avicel PH102) | 50.75 |
| 23. Stearic Acid | 4.00 |
| 24. Magnesium Stearate | 8.00 |
| TOTAL TABLET WEIGHT (mg) | 1463.50 |

[1]Beta carotene input was based on actual assay.

TABLET MANUFACTURING PROCEDURE

1. Mix items 4–11. Mill through a hammer mill having a #0 plate, hammers at medium speed. Remix and set aside as part A.
2. Mix items 1, 2, and 3. Set aside as part B.
3. Mix items 12–17. Set hammer mill to use knives. Mill through a #0 plate, knives at medium speed. Remix and set aside as part C.
4. Mix parts A, B, and C with items 18, 20, 21, and 22 for 10 minutes. Add and mix item 19. Mix for 10 minutes.
5. Add items 23 and 24 as a premix with a screened (through 30 mesh) portion of the blend. Mix for 2 minutes.
6. Compress at 3 tons on Stokes Single Punch Instrumented Tablet Press with 5/16"×3/4" capsule-shaped punches.
7. Mix 23 and 243. Screen through 30 mesh and mix with the material from step 4 for two minutes.

EXAMPLE 8

MULTIVITAMIN TABLETS WITH IRON FORMULATION

| Ingredients | mg/tablet |
|---|---|
| 1. Acetabeads Type 500A | 2.70 |
| 2. Acetabeads Type 500A/50D3 | 10.80 |
| 3. Beta Carotene 20% Beadlets | 20.25[1] |
| 4. Dry Vitamin E Acetate 50% SD | 66.00 |
| 5. Ascorbic Acid 90% Granulation | 80.00 |
| 6. Folic Acid | 0.50 |
| 7. Thiamine Mononitrate | 1.73 |
| 8. Riboflavin Type S | 1.87 |
| 9. Niacinamide Free Flowing | 22.00 |
| 10. Pyridoxine Hydrochloride | 2.67 |
| 11. Vitamin B12 0.1% SD | 7.50 |
| 12. BITRIT-1 | 16.50 |
| 13. Calcium Pantothenate | 14.00 |
| 14. Ferrous Fumarate (32.87% Fe) | 54.70 |
| 15. Corn Starch (Sta-Rx 1500) | 20.00 |
| 16. Microcrystalline Cellulose (Avicel PH102) | 60.00 |

-continued

MULTIVITAMIN TABLETS WITH IRON FORMULATION

| Ingredients | mg/tablet |
|---|---|
| 17. Dicalcium Phosphate Dihydrate, Unmilled | 37.03 |
| 18. Magnesium Stearate | 2.00 |
| TOTAL TABLET WEIGHT (mg) | 420.25 |

[1]Beta carotene input was based on actual assay.

TABLET MANUFACTURING PROCEDURE

1. Blend items 6, 7, 8, 10, 11, and 12 for 5 minutes. Add items 9 and 15. Mix for 10 minutes. Mill through a #1A plate, medium speed with knives forward.
2. Add items 1, 2, 3, and 13 as a premix with a portion of the blend. Mix for 10 minutes.
3. Add items 4, 5, 14, 16, and 17. Mix for 10 minutes.
4. Screen a portion of mixture from step 3 through a 30 mesh screen and mix with item 18. Mix this combination with the remainder of the step 3 mixture for 2 minutes.
5. Compress at 2 tons on Stokes Single Punch Instrumented Tablet Press using 3/8" D.C. punch at rate of 52 tablets/min.

EXAMPLE 9

Procedure for Tinctorial Power

Ca. 100 mg powder (or emulsion) is accurately weighed into a 100 ml 15 volumetric flask and dissolved in ca. 50 ml of distilled water at 50° C. Sonicate 5 min. Subsequently, the emulsion is cooled and filled to the mark with distilled water. 5 ml of this solution is diluted with distilled water to give 100 ml (=test solution). This test solution is analyzed in the spectrophotometer against a water blank at 200 nm to 650 nm. The photometer analysis should be performed as rapidly as possible after the preparation of the solutions. If the analysis is not performed in amber glassware, the work should be performed away from bright lights.

The maximum absorptivity (E) occurring at a wavelength ($\lambda$max) between 450–500 nm and corrected for the absorptivity at 650 nm is used to calculate the $E_1^1$ in water which is taken as a measure of the tintorial power or color intensity. This is calculated, as follows:

$$E_{1cm}^{1\%} = \frac{E_{max\lambda} \times 1000 \times 100 \times 100}{\text{Sample wt. (mg)} \times 5 \times \beta - \text{carotene content}}.$$

What is claimed is:
1. A process for the manufacture of a solid carotenoid powder containing carotenoid beadlets, the process comprising:
   1) melting an aqueous suspension containing
      (a) carotenoid crystals in an amount sufficient to provide 10% to 25% by weight in a solid carotenoid powder,
      (b) a surfactant in an amount sufficient to provide 0.1% to 6% by weight in the solid carotenoid powder, and
      (c) a protective colloid in an amount sufficient to provide 5% to 75% by weight in the solid carotenoid powder in a heat exchanger wherein the residence time of the carotenoid crystals in the heat exchanger is less than 60 seconds;

2) homogenizing the melted aqueous carotenoid suspension at a pressure of 1,400 to 40,000 p.s.i. to obtain a carotenoid emulsion; and 3) converting the carotenoid emulsion into a dry powder by a spray process, thereby forming a solid carotenoid powder containing carotenoid beadlets having a matrix with a mean particle size of carotenoid particles within the beadlet matrix from 0.1 to 0.5 microns.

2. The process of claim 1 wherein said pressure is in the range from 1,400 to 15,000 psi.

3. The process of claim 2 wherein said carotenoid is β-carotene.

4. The process of claim 3 wherein the tem is in the range from 180° C. to 250° C.

5. The process of claim 4 wherein the temperature of melting is in the range from 180° C. to 225° C.

6. The process of claim 5 wherein said temperature is in the range from 185° C. to 195° C.

7. The process of claim 6 wherein said pressure is in the range from 2000 to 10,000 psi.

8. A process for the manufacture of a solid carotenoid powder containing carotenoid beadlets, the process comprising:

1) melting an aqueous suspension containing (a) carotenoid crystals in an amount sufficient to provide 10% to 25% by weight in a solid carotenoid powder, (b) a surfactant in an amount sufficient to provide 0.1% to 6% by weight in the solid carotenoid powder, and (c) a protective colloid in an amount sufficient to provide 5% to 75% by weight in the solid carotenoid powder in a first heat exchanger, wherein the residence time of the carotenoid crystals in the first heat exchanger is less than 60 seconds, followed by melting in a second heat exchanger, wherein the residence time of the carotenoid crystals in the second heat exchanger is less than 3 seconds;

2) homogenizing the melted aqueous carotenoid suspension at a pressure of 1,400 to 40,000 p.s.i. to obtain a carotenoid emulsion; and 3) converting the carotenoid emulsion into a dry powder by a spray process, thereby forming a solid carotenoid powder containing carotenoid beadlets having a matrix with a mean particle size of carotenoid particles within the beadlet matrix from 0.1 to 0.5 microns.

* * * * *

UNITED STATES PATENT AND TRADEMARK OFFICE
CERTIFICATE OF CORRECTION

PATENT NO : 6,093,348
DATED : July 25, 2000
INVENTOR(S) : Ray Edward KOWALSKI, et al.

It is certified that error appears in the above-identified patent and that said Letters Patent are hereby corrected as shown below:

On the title page, under [73] Assignee, please change "Nutley" to --Parsippany--;

Column 13, line 13 (line 1 of claim 4), please delete "tem" and insert therefor --temperature of melting--.

Signed and Sealed this

Twenty-fourth Day of April, 2001

Attest:

NICHOLAS P. GODICI

Attesting Officer

Acting Director of the United States Patent and Trademark Office